(12) United States Patent
Sanders

(10) Patent No.: US 12,403,108 B2
(45) Date of Patent: Sep. 2, 2025

(54) NON-ENZYMATIC DEBRIDING AGENT AND METHOD OF USE THEREOF

(71) Applicant: CMC Consulting Boston, Inc., Framingham, MA (US)

(72) Inventor: Mitchell Sanders, Grafton, MA (US)

(73) Assignee: Alira Health Boston LLC, Framingham, MA (US)

( * ) Notice: Subject to any disclaimer, the term of this patent is extended or adjusted under 35 U.S.C. 154(b) by 178 days.

(21) Appl. No.: 15/628,908

(22) Filed: Jun. 21, 2017

(65) Prior Publication Data

US 2020/0268695 A1 Aug. 27, 2020

Related U.S. Application Data

(63) Continuation of application No. PCT/US2015/067521, filed on Dec. 22, 2015.
(Continued)

(51) Int. Cl.
*A61K 31/17* (2006.01)
*A61K 9/06* (2006.01)
(Continued)

(52) U.S. Cl.
CPC ............... *A61K 31/17* (2013.01); *A61K 9/06* (2013.01); *A61K 38/08* (2013.01); *A61K 47/02* (2013.01);
(Continued)

(58) Field of Classification Search
CPC .. A61K 2300/00; A61K 31/155; A61K 31/17; A61K 31/7016; A61K 38/08;
(Continued)

(56) References Cited

U.S. PATENT DOCUMENTS 6,201,164 B1 3/2001 Wulff et al.
2003/0198631 A1 10/2003 Shi et al.
(Continued)

OTHER PUBLICATIONS

Uptima (HECAMEG, Glucose based detergent, 785480.pdf (interchim.fr), Nov. 2003).*
(Continued)

*Primary Examiner* — Jeffrey S Lundgren
*Assistant Examiner* — Anthony Joseph Seitz
(74) *Attorney, Agent, or Firm* — Brian M. Dingman; Prince Lobel Tye LLP

(57) ABSTRACT

A non-enzymatic debridement agent that is less expensive, less cytotoxic, and more effective than enzymatic and sharp surgical debridement of eschar material. The non-enzymatic debridement agent is based on a formulation of detergent with a high critical micelle concentration and a denaturing agent along with an optional optimized buffer. The non-enzymatic wound debriding agent is able to dissolve eschar material in under one week. The buffer or ointment may contain an optimized pH, salt concentration, reducing agent, and other components that aid in the debridement of eschar material from chronic wounds and burn wounds. The non-enzymatic debridement agent can be formulated as an ointment, liquid rinse under pressure, and/or as a combination product with an advanced wound dressing that can act as a sink to remove the solubilized eschar material from the surface of the wound to assist in the debridment and proper healing of wounds.

20 Claims, 6 Drawing Sheets

Specification includes a Sequence Listing.

Related U.S. Application Data

(60) Provisional application No. 62/095,220, filed on Dec. 22, 2014.

(51) Int. Cl.
| | | |
|---|---|---|
| *A61K 38/08* | (2019.01) | |
| *A61K 47/02* | (2006.01) | |
| *A61K 47/20* | (2006.01) | |
| *A61K 47/26* | (2006.01) | |
| *A61K 47/42* | (2017.01) | |

(52) U.S. Cl.
CPC .............. *A61K 47/20* (2013.01); *A61K 47/26* (2013.01); *A61K 47/42* (2013.01)

(58) Field of Classification Search
CPC ........ A61K 38/10; A61K 45/06; A61K 47/02; A61K 47/20; A61K 47/26; A61K 47/36; A61K 47/42; A61K 9/0019; A61K 9/06; A61P 17/00; A61P 17/02; A61P 31/04; A61P 41/00
See application file for complete search history.

(56) References Cited

U.S. PATENT DOCUMENTS

| | | |
|---|---|---|
| 2005/0281806 A1 | 12/2005 | Trumbore et al. |
| 2006/0205646 A1 | 9/2006 | Sanders et al. |
| 2009/0010910 A1* | 1/2009 | Toren ................... A61K 33/38 |
| | | 424/94.1 |

OTHER PUBLICATIONS

Mishra, R.K., Photosynthetica 47, 451-456 (2009) (Year: 2009).*

The International Preliminary Report on Patentability issued on Jun. 27, 2017 by the International Bureau for PCT Application No. PCT/US2015/067521.

The Written Opinion of the International Searching Authority mailed Jun. 10, 2016 for PCT Application No. PCT/US2015/067521.

The International Search Report issued by the International Searching Authority mailed Jun. 10, 2016 for PCT Application No. PCT/US2015/067521.

* cited by examiner

SEQUENCE LISTING

```
<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 1

Val Val Val Val Val Val Asp
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 2

Val Val Val Val Val Val Lys
1               5

<210> SEQ ID NO 3
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 3

Pro Phe Pro Gln Ala Asn Tyr Ile Thr Tyr Cys
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 4

Glu Gly Ala Met Phe Leu Glu Ala Ala Ile Pro Met Ser Lys
1               5                   10
```

NON-ENZYMATIC DEBRIDING AGENT AND METHOD OF USE THEREOF

CROSS-REFERENCE TO RELATED APPLICATION

This application is a continuation of and claims priority of PCT/US2015/067521, filed on 22 Dec. 2015, which itself claimed priority of Provisional application 62/095,220, filed on 22 Dec. 2014.

INCORPORATION BY REFERENCE

Incorporate by reference herein the "Sequence Listing" filed on Apr. 14, 2025. The file is identified as follows: Title: "695 Sequence Project listing FINAL_ST25"; Date of Creation: Apr. 10, 2025; Size: 1,120 bytes.

TECHNICAL FIELD

This invention relates to the field of wound care, wound repair, and tissue regeneration. There may be additional dermal and medical applications of this formulation. The primary indications are the non-enzymatic debridement of chronic wounds, acute wounds, and burn wounds. However secondary applications include reconstructive surgery and tissue remodeling.

BACKGROUND ART

Chronic wounds often have necrotic tissue (hard black eschar and yellow slough) that needs to be removed prior to the initiation of proper wound healing. Current well-adopted methods include enzymatic debridement and sharp surgical debridement. There are other methods that are used for debridement including using fly maggots and mechanical debridement (water under pressure, biodegradable glass-based composition containing $B_2O_3$, ultrasound waves, and lasers). Although these latter methods have some technical merit, they are rarely used in the field, and thus, will not be the primary comparator for developing innovative methods for wound debridement.

SUMMARY OF INVENTION

Technical Problem

Enzymatic debridement is performed with a protease such as collagenase, bromelain, Seaprose or papain. The disadvantages of enzymatic debridement include: the treatment is expensive ($250 per tube, $4000 per treatment), it requires a prescription and the enzymatic debridement causes inflammation and significant discomfort. In some instances, patients treated with collagenase experience redness (erythema) around the edge of the wound bed, significant irritation in highly exudative wounds, and after extended use, hypersensitivity due to a mild allergic reaction (pruritus).

In the case of surgical debridement, the operating room (OR) procedure requires the use of a scalpel, forceps, and scissors to scrape off the necrotic tissue from the wound. The major disadvantages of surgical debridement include pain and the cost associated with an OR visit. In a recent double blind randomized and controlled clinical trial, it was determined that surgical debridement alone may be insufficient to debride and heal chronic wounds. At the 2014 Fall Symposium for Advanced Wound Care, key opinion leaders were recommending the use of collagenase in combination with surgical debridement. Clearly new methods are required to improve the health economics of debriding chronic wounds. The ideal method should cost less than the currently preferred methods, and improve the quality of life of the patient through the use of a method that works better than enzymatic debridement and has less adverse side effects (e.g. reduced erythema, pain, and pruritus).

Solution to Problem

A novel non-enzymatic approach to debride chronic wounds that uses a gentle non-ionic detergent with a high critical micelle concentration in combination with a natural denaturing agent that allows for the necrotic material to be denatured and dissolved, which then allows it to be wicked into an advanced wound dressing. The mechanism of action involves a three-step process to non-enzymatically debride the necrotic eschar material. The first step involves rehydration and denaturation of the necrotic material with a denaturant. Exemplary denaturants include (but are not limited to) urea, urea derivatives, and/or guanidine HCL. The denaturant may also contain a mimetic peptide that can disrupt (reduce) disulfide bonds of cysteines from the necrotic tissue. The second step involves the solubilization of the denatured material, such as by a gentle detergent with a high critical micelle concentration (High CMC). The high CMC is advantageous because in step three this material can be easily wicked away from the surface into a wound dressing that can be used with moderate to highly exudative wounds.

The non-enzymatic debriding agent may also include a preferred buffer, pH, and ionic strength (salt concentration). An embodiment also includes micro or nano particles that have been shown to accelerate the dissolution time by gentle mechanical disruption of the tissue. In some instances, citric acid and sodium bicarbonate or ammonium bicarbonate may be included to assist in the gentle agitation of the active ingredients. An embodiment includes the use of a moderate to highly absorbent wound dressing such as a foam or hydrocolloid dressing that can wick the dissolved eschar material from the wound bed. In another embodiment, the solution is provided in a liquid form with or without pressure to rapidly dissolve the eschar. In a third embodiment, the formulation is mixed in a gel such as xanthan gum, polyethylene glycol, xylose, hydroxyl ethyl cellulose, or petroleum jelly to keep a high concentration of the non-enzymatic debriding agent at the site required for debridement before it is wicked away by a moderate to highly absorbent dressing. The non enzymatic debriding agent may be used in combination with an antimicrobial dressing such as silver sulfadiazine, chlorohexadine, hypochlorous acid (0.01%), or a Manuka honey formulation. It is also envisioned that this agent could be used in combination with negative pressure wound therapy (NPWT).

A benefit of the high critical micelle concentration of the detergent (>19 mM) is that it allows easy removal through exudate passing through the dressing. The detergent dissociates aggregated proteins in the eschar and slough but does not denature proteins because it is not charged. A gentle non-ionic detergent can have a sugar, peptide, or other backbone to improve solubility in wound fluid. Examples of a gentle nonionic sugar based detergent include but are not limited to 6-O—(N-Heptylcarbamoyl)-methyl-α-D-glucopyranoside and Methyl-6-O—(N-heptylcarbamoyl)-α-D-glucopyranoside referred to as HECAMEG. Peptides can be synthesized with gentle detergent-like properties, and these are commonly referred to as peptergents. Peptergents are small self-assembling peptides with detergent properties that represent a phospholipid-like molecule. An example of a peptergent includes VVVVVVD (SEQ ID NO: 1). The valine (V) acts as a non-polar tail. The $V_6D$ resembles a phospholipid molecule of approximately 2 nm in length. Peptergents can be added in combination with a sugar-based detergent to form mixed micelles that have interesting solubilization characteristics. In another embodiment, the peptide can include the sequence PFPQANYITYC (SEQ ID NO: 3) in the D configuration to act as a sink to remove human neutrophil elastase which may reduce the inflammation in a chronic wound. Alternatively, EGAMFLEA-AIPMSK (SEQ ID NO: 4) could be added in a D configuration to bind bacterial protease that can interfere with wound healing. In another embodiment, the peptergent has a peptide or phosphine like moiety that acts to reduce the cysteines of the denatured eschar material in a similar mode of action as dithiothreitol, beta mercatoethanol or tris(2-carboxyethyl)phosphine (TCEP).

The detergents can be solubilized in a weak denaturant such as 50-250 mM urea, guanidine HCL, or plant derived urea compounds that are generally recognized as safe (GRAS) and commonly used in cosmetics.

Advantageous Effects of Invention

An inexpensive, gentle and effective wound debridement agent that uses the power of a denaturant with a gentle detergent with a high CMC to dissolve the eschar material in less than 14 days based on an in vitro model system that uses "burnt ends" from a beef brisket to demonstrate its effectiveness. This dissolution time is 13 days faster than the commercially available enzymatic debriding agent from Smith and Nephew (Santyl®). Similar dissolution results were observed with sharp debrided human eschar material.

This disclosure features a method of debriding a wound with a non enzymatic debriding agent, and the non enzymatic wound debriding agent itself. The active ingredients may include a denaturant, a gentle detergent with a high critical micelle concentration (CMC) and an optimized reducing and physiological buffer. Examples of the denaturant include urea, guanidine HCL, or a synthetic animal or plant derived derivative of urea or guanidine HCL. Examples of the detergent include detergents with a glycosidic headgroup, including but not limited to alkyl β-glucosides and alkyl β-maltosides, with alkyl chain lengths typically ranging from 8 to 14. The detergent may be peptide based (peptergent) but has detergent like properties, including but not limited to VVVVVVD (SEQ ID NO: 1). The detergent may be a mixture of glycosidic and peptergent components. The peptide or mimetic peptide like molecule may also have reducing properties of a mercaptan or non-mercaptan reducing agent.

The detergent may have similar properties of being gentle and having a high CMC including but not limited to digitonin, methylglucamides (MEGA-8 to MEGA-10), polyethylene glycol, and N,N-dimethyldodecylamine-N-oxide (DDAO; also called N,N-lauryldimethylamine-N-oxide or LDAO). The peptergent may be in the D configuration to prevent proteolysis during dissolution of the eschar material. Alternatively the peptide may be used to identify a chemical with a similar structure and characteristics of a high CMC detergent and denaturant. The buffer formula may include a neutral physiological buffer such N-2-aminoethanesulfonic acid (ACES), Phosphate Buffered Saline (PBS), or 2-(N-morpholino)ethanesulfonic acid (MES) at a concentration of, for example, 10-200 mM. The buffer formula may also include sodium chloride (NaCl), for example at 100-200 mM. The buffer formula may also include citric acid and/or sodium bicarbonate to agitate the exudate solution to enhance the dissolution time.

The buffer formula may also include a nano or micro fiber, nanochannel, or nanosphere to aid in the dissolution of the eschar material. The fiber may comprise silica, gelatin with a high bloom number, microspheres or crystalline materials including simple and complex sugars. The fiber may comprise single or multiwall calcium carbonate nanospheres or nanochannels, carbon nanotube, carbon buckyball, gold or silver nanoparticles, titanium dioxide ($TiO_2$), or quantum dots, wherein the quantum dots are nanosized crystals of various elements (e.g., silicon and germanium, cadmium and selenium).

The debriding agent may be used in a gel or ointment with or without a wound dressing covering. The debriding agent may be used in combination with an antimicrobial and antibiotic solution, gel, or ointment. Ointments include xanthan gum, polyethylene glycol, and petroleum based ointments.

DESCRIPTION OF EMBODIMENTS

It is envisioned that there will be at least three different embodiments (product formulations) of the subject non-enzymatic debriding agent. One is a dressing. The choice of dressing would be a moderate to highly absorbent material such a foam, hydrocolloid dressing, or biocomposite dressing. Although the dressing acts to wick away the dissolved ecshar material it is envisioned that negative pressure wound therapy (NPWT) could be another approach to remove the eschar material. A second embodiment is an ointment. The ointment would likely contain a thickening agent such as white petrolatum USP, xanthan gum or polyethylene glycol, for example. This formulation could be used in combination with an antibiotic or antimicrobial dressing, aqueous solution, gel, hydrogel, or ointment. It would be counter indicated with a collagen dressing because the non enzymatic wound debriding agent would denature the collagen. A third embodiment of the formulation is a liquid rinse under pressure to aid in the dissolution of the eschar material. Combinations of these embodiments are also included (e.g. a gel formulation used under a dressing or a dressing that is adapted to receive a rinse of the liquid formulation under positive or negative pressure).

Figure 1:
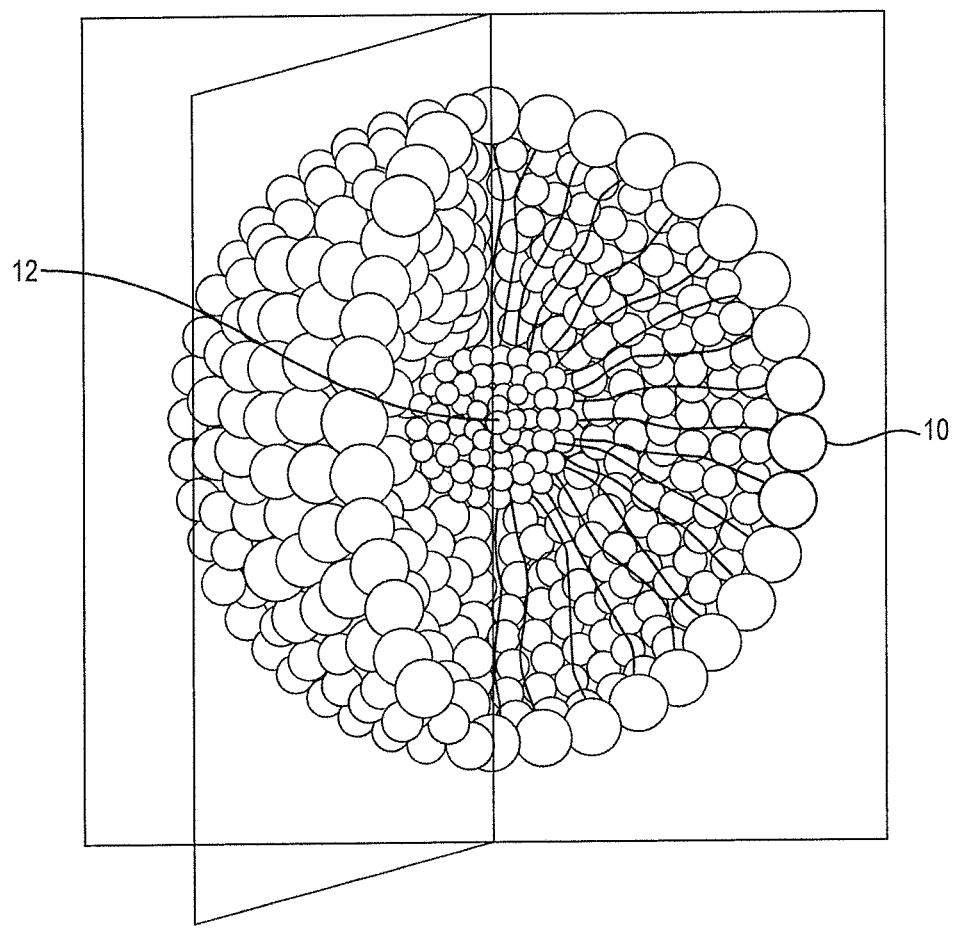
FIG. 1 is a diagram of active components of an example of the non enzymatic wound debridement agent. Other active components are not added to the drawing for simplicity.

FIG. 1 is a diagram of active components of an example of the non enzymatic wound debridement agent that can be used to dissolve eschar material. The active ingredients include a lipid shell with a high critical micelle concentration 10 to dissolve eschar material, and a hydrophilic denaturing core 12 that includes urea or similar gentle eschar denaturant. Other active components can include a physiological buffer, salt, bicarbonate, citric acid, a reducing agent, denaturant, and/or micro/nano particles to aid in the dissolution of the eschar material. The other active components are not added to the drawing for simplicity.

Figure 2A:
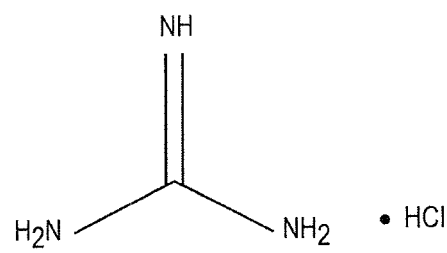
FIG. 2A illustrates the chemical structure of urea.
Figure 2B:
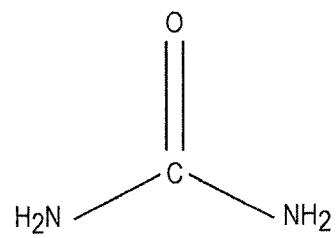
FIG. 2B illustrates the chemical structure of guanidine hydrochloride.

In FIGS. 2A and 2B are the chemical structure of two denaturants that can be used herein: urea (FIG. 2A) and guanidine hydrochloride (FIG. 2B). Other synthetic, plant or animal derived denaturants may also be used and are within the scope of the present disclosure. Examples include but are not limited to carbamide peroxide, allantoin, andhydantoin, thiol urea and dimethyl urea.

Figure 3A:
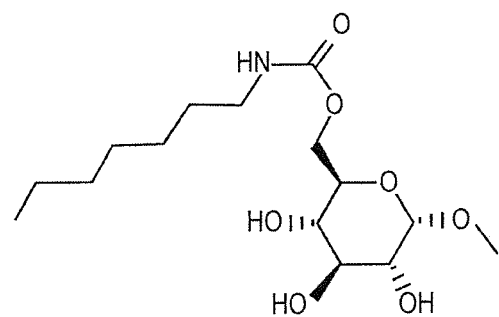
FIG. 3A illustrates the chemical structure of HECAMEG detergent.
Figure 3B:
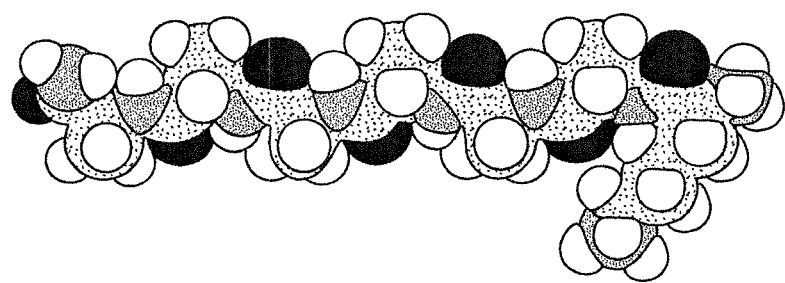
FIG. 3B illustrates the chemical structure of peptide with lipid-like properties (VVVVVVK) (SEQ ID NO: 2) referred to as a peptergent.

In FIGS. 3A and 3B are the chemical structure of HECAMEG detergent (FIG. 3A) (a glucose-based detergent from Enzo Life Sciences, Inc. of Farmingdale, NY, USA) and a peptide with lipid-like properties referred to as a peptergent (FIG. 3B) (VVVVVVK) (SEQ ID NO: 2). Both have a polar head group and a hydrophobic tail so that they can form micelles. Both HECAMEG and peptergents are gentle detergents with a high CMC that have been used to isolate membrane bound proteins in their native conformation for biochemistry and crystallography studies.

The non enzymatic debriding agent could be placed on the absorbent or adhesive layer of a wound dressing. Alternatively the non-enzymatic debriding agent could be supplied in petroleum jelly or ointment like formulation. Preferred ointments include xanthan gum (XG), polyethylene glycol (PEG), and petroleum jelly. Another alternative is to apply as a liquid, for example by application or by spraying.

An in vitro model system was developed to study the dissolution of eschar like material using burnt ends from a beef brisket. A beef brisket was cooked for 8 hours at 150° C. The burnt ends were cut into small rectangular pieces and then weighed. A burnt piece weighing approximately 250 mg was placed in a 1.5 mL microcentrifuge tube and incubated with 1 mL of the present debridement solution, with gentle rotation until the material was completely dissolved. It was determined that it is possible to dissolve the eschar material in 7 days which is three times faster than a FDA-cleared enzymatic debriding agent (Santyl). It is believed that the subject non-enzymatic product formulation is less expensive, more active, and much more gentle than surgical and enzymatic debridement methods.

Figure 4:
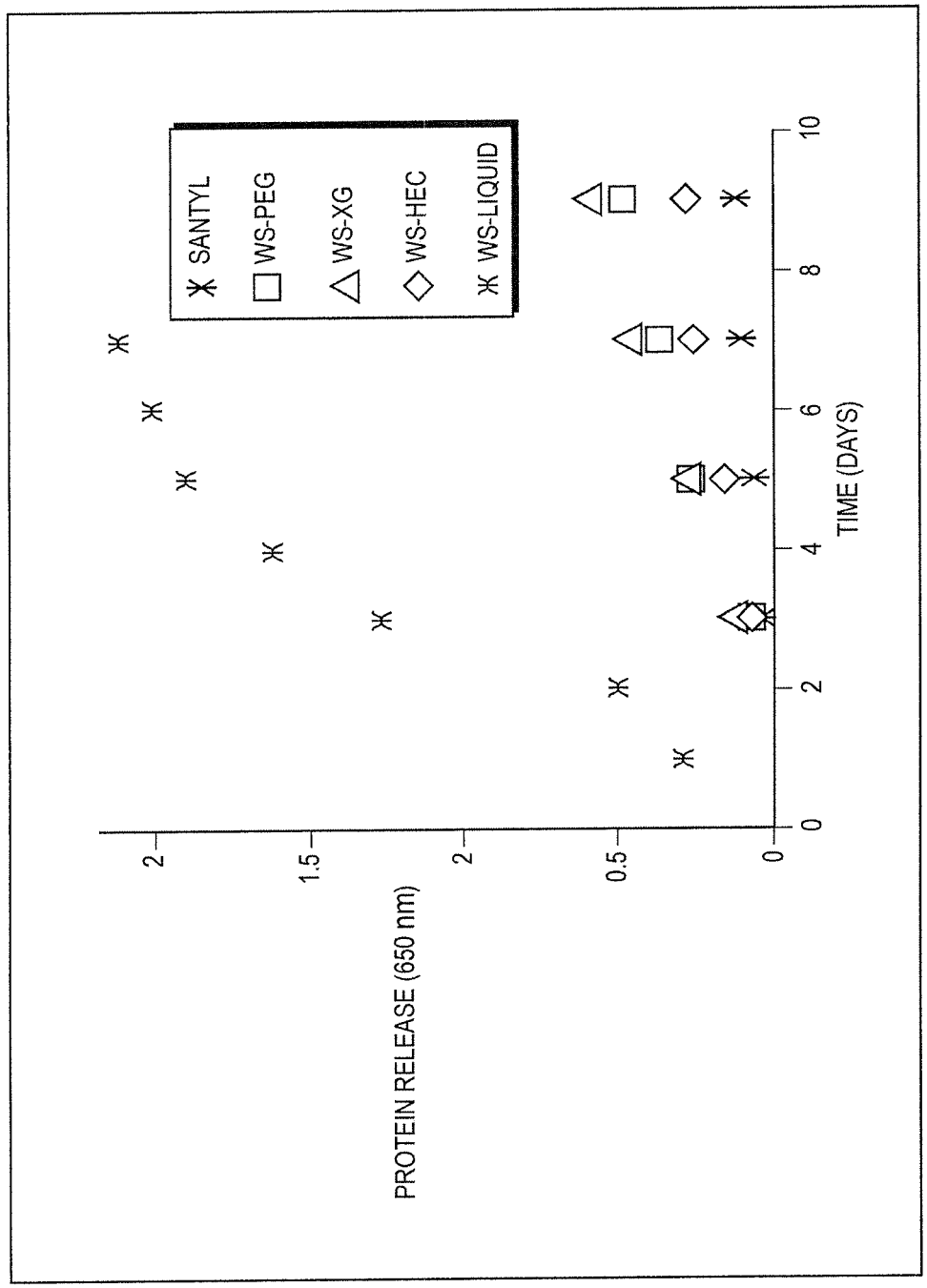
FIG. 4 gives results of an in vitro testing of sharp debrided human eschar material in comparison with different liquid and gel formulations of the non enzymatic wound debriding agent.

FIG. 4 gives results of an in vitro testing of sharp debrided human eschar material in comparison with different liquid and gel formulations of the non enzymatic wound debriding agent. Fresh frozen sharp debrided human eschar material was kindly provided by the Dr. Tom Serena of the Serena Group. The material was cut into uniform pieces and then treated with different liquid and gel formulations of the non-enzymatic debriding agent. The non-enzymatic debridement agent formulation is 3-10× more effective and three times faster than a FDA-cleared enzymatic debriding agent (Santyl).

Figure 5:
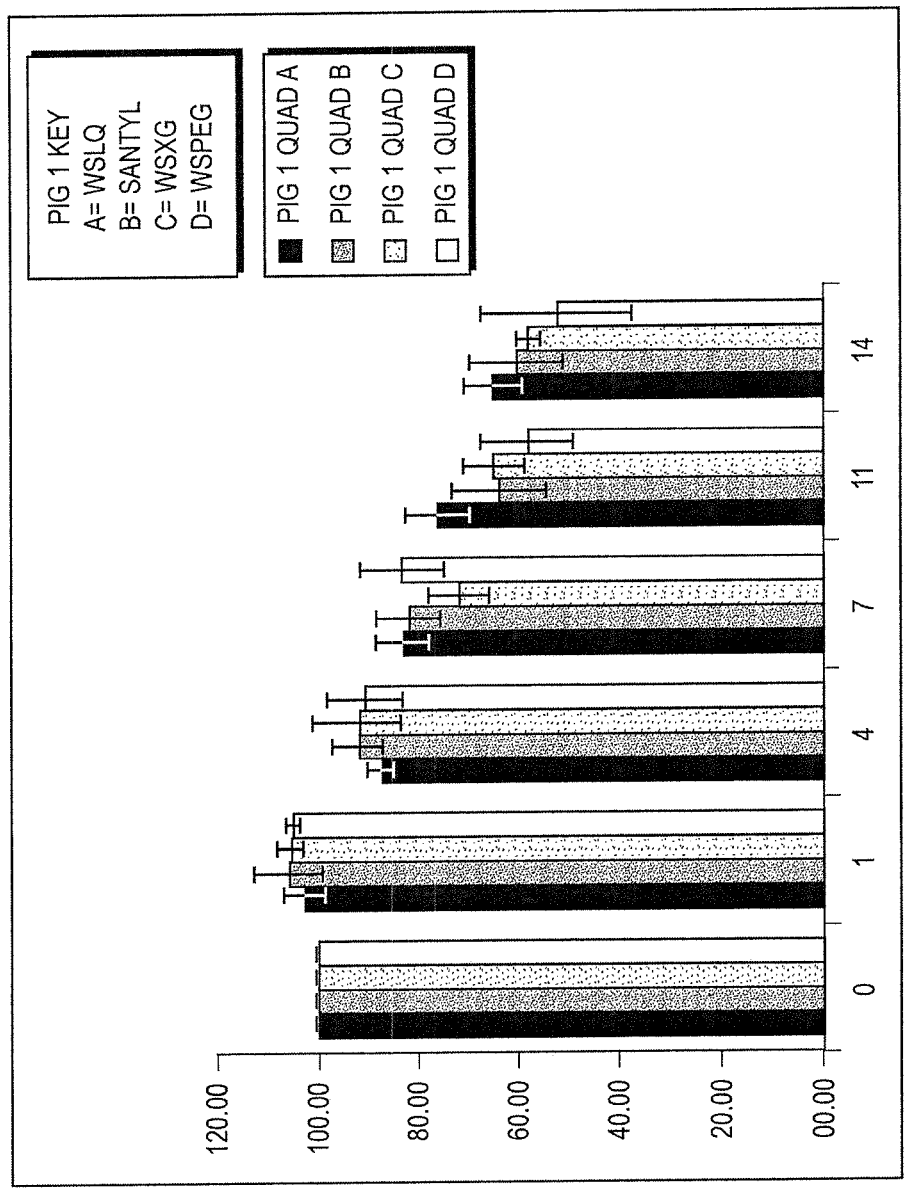
FIG. 5 gives results (average wound size) of a soft eschar porcine model used to test the liquid and gel formulations of the non enzymatic debriding agent in comparison with a FDA-cleared enzymatic debriding agent.
Figure 6:
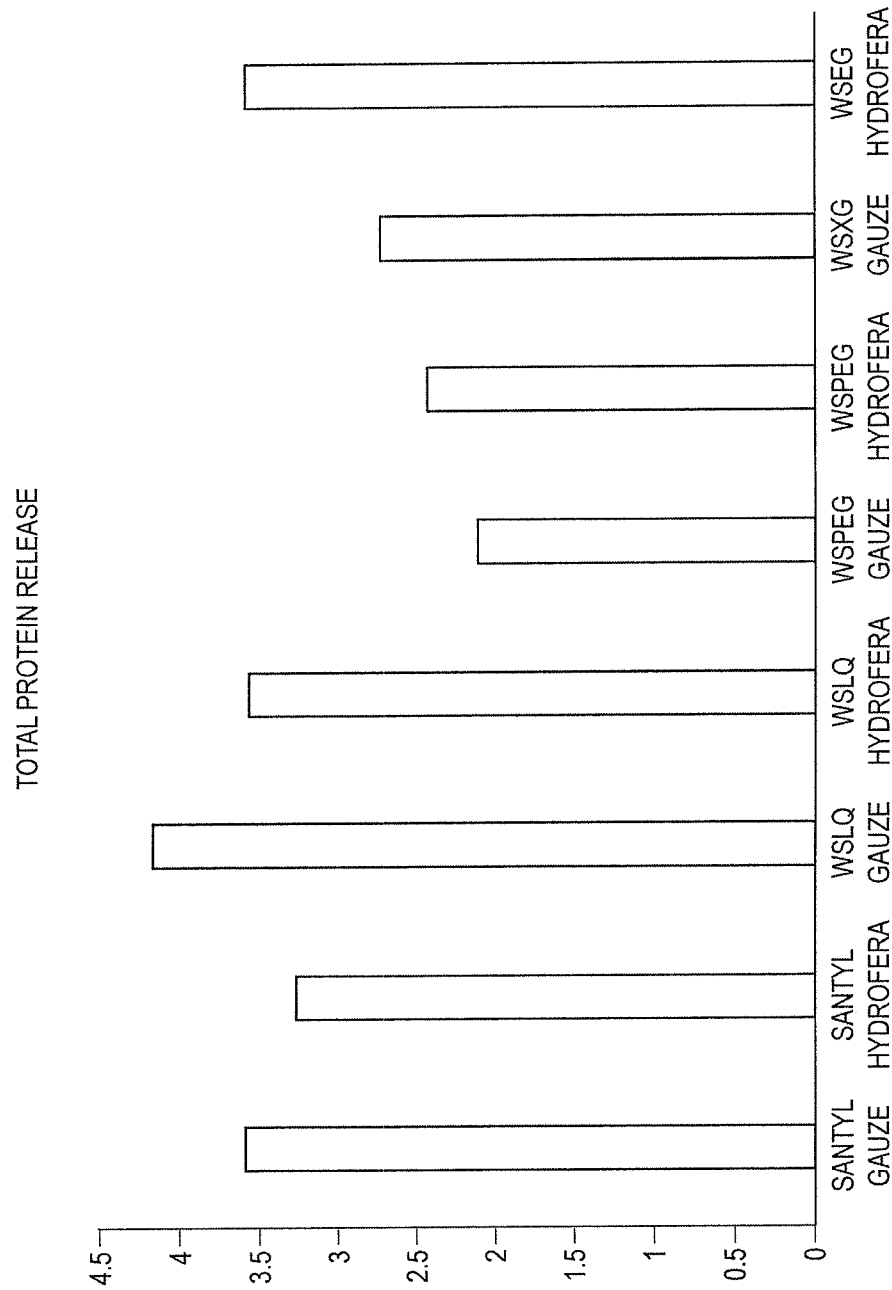
FIG. 6 gives total protein released from the porcine model of FIG. 5, for two prior art formulations and six present non enzymatic debriding agents.

In FIG. 5 a soft eschar porcine model was used to test the liquid and gel formulations of the non enzymatic debriding agent in comparison with a FDA-cleared enzymatic debriding agent (Santyl). Results indicate that the non enzymatic debriding agent is equally effective at healing. FIG. 6 gives results in terms of the removal of eschar material (based on protein release) in the porcine soft eschar model (Shi et al., 2009: Wound Repair Regen. 2009 November-December; 17(6):853-62). To measure protein release from the pig studies the wound dressings (gauze or Hydrofera Blue dressing from Hollister Woundcare of Libertyville, IL, USA) were extracted with 5 ml of PBS buffer while rotating overnight and then the total protein content was measured with a Bio-Rad Coomassie blue (G-250) dye binding assay (Bradford, 1976).

In FIGS. 4-6 "WS" is an acronym for the non enzymatic wound debriding agent used. "LQ" is a liquid version. "XG" is a xanthan gum version, "PEG" is a version with PEG, and "HEC" is a version with hydroxyethyl cellulose. Formulations used to gather the data are described below.

Formulations

The liquid form includes 50-250 mM Hecameg, 100-500 mM Urea, 5-250 mM NaCl, 10-200 mM ACES (N-(2-Acetamido)-2-Aminoethane Sulfonic Acid) buffer, and 1-10 mM TCEP (Tris(2-carboxyethyl)phosphine hydrochloride). The components are mixed in sterile water, then sterile filtered in a biosafety cabinet. Put the tip of a sterile syringe in the liquid and pull back the plunger until the desired amount is in the syringe and then cap the syringe and place the holder on the plunger. Fill the syringes in the biosafety cabinet to ensure sterility.

Gel formulations include one of the following ointments: 1-20% Xanthan Gum, 10-30% polyethylene glycol (60% PEG 400, 40% PEG 3500), 1-10% hydroxyethyl cellulose (HEC), or 10-30% petroleum jelly (white petrolatum). The gel formulations are sterilized by gamma sterilization 25 kGa.

INDUSTRIAL APPLICABILITY

A novel non-enzymatic wound debridement agent based on a proprietary formulation to dissolve eschar material. The agent is gentle and inexpensive enough to be incorporated into an advanced wound dressing. The clear industrial advantages over enzymatic or surgical wound debridement include but are not limited to: proprietary formulation, less painful than sharp debridement, less expensive than enzymatic debridement, not a drug but a detergent impregnated dressing, suggested US regulatory path: Class IIB Medical Device.

A number of implementations have been described. Nevertheless, it will be understood that additional modifications may be made without departing from the scope of the inventive concepts described herein, and, accordingly, other embodiments are within the scope of the following claims.

What is claimed is:

1. A non-enzymatic wound debriding agent for application to necrotic human tissue that includes eschar that develops slough, comprising:
   100-500 mM urea;
   a gentle detergent with a high critical micelle concentration (CMC) of greater than 19 mM, wherein the micelles have hydrophilic denaturing cores that include the urea;
   sodium chloride;
   a physiological buffer; and
   water.

2. The non-enzymatic wound debriding agent of claim 1, wherein the detergent comprises a glycosidic headgroup comprising one or more of alkyl β-glucosides and alkyl β-maltosides, with alkyl chain lengths ranging from 8 to 14.

3. The non-enzymatic wound debriding agent of claim 1, wherein the detergent comprises a peptide based peptergent that has detergent like properties.

4. The non-enzymatic wound debriding agent of claim 1, wherein the detergent comprises a glycosidic headgroup comprising one or more of alkyl β-glucosides and alkyl β-maltosides, with alkyl chain lengths ranging from 8 to 14, and a peptide based peptergent that has detergent like properties.

5. The non-enzymatic wound debriding agent of claim 1, wherein the detergent is a HECAMEG detergent.

6. The non-enzymatic wound debriding agent of claim 1, wherein the buffer comprises one or more of N-2-aminoethanesulfonic acid (ACES), Phosphate Buffered Saline (PBS), and 2-(N-morpholino) ethanesulfonic acid (MES) at a concentration of 10-200 mM.

7. The non-enzymatic wound debriding agent of claim 1, in a gel or ointment.

8. The non-enzymatic wound debriding agent of claim 1, that is part of an antimicrobial and antibiotic solution, gel, or ointment, where the gel or ointment comprises xanthan gum, polyethylene glycol, or is petroleum based.

9. The non-enzymatic wound debriding agent of claim 8, where the solution, gel or ointment further comprises a non mercaptan reducing agent that comprises a peptide or peptide like molecule.

10. The non-enzymatic wound debriding agent of claim 9, where the detergent comprises a non mercaptan reducing disulfide moiety.

11. A method of debriding a wound, comprising:
applying to the wound a non-enzymatic wound debriding agent that comprises:
a micelle formulation comprising 100-500 mM urea;
a gentle detergent with a high critical micelle concentration (CMC) of greater than 19 mM, wherein the micelles have hydrophilic denaturing cores that include the urea;
sodium chloride;
a physiological buffer; and
water.

12. The method of claim 11, wherein the detergent comprises a glycosidic headgroup comprising one or more of alkyl β-glucosides and alkyl β-maltosides, with alkyl chain lengths ranging from 8 to 14.

13. The method of claim 11, wherein the detergent comprises a peptide based peptergent that has detergent like properties.

14. The method of claim 11, wherein the detergent comprises a glycosidic headgroup comprising one or more of alkyl β-glucosides and alkyl β-maltosides, with alkyl chain lengths ranging from 8 to 14, and a peptide based peptergent that has detergent like properties.

15. The method of claim 11, wherein the detergent is a HECAMEG detergent having a CMC of greater than 19 mM, in the D configuration to inhibit proteolysis during dissolution of eschar material.

16. The method of claim 11, wherein the buffer comprises one or more of N-2-aminoethanesulfonic acid (ACES), Phosphate Buffered Saline (PBS), and 2-(N-morpholino) ethanesulfonic acid (MES) at a concentration of 10-200 mM.

17. The method of claim 11, wherein the wound debriding agent is in a gel or ointment.

18. The method of claim 11, wherein the wound debriding agent is part of an antimicrobial and antibiotic solution, gel, or ointment, where the gel or ointment comprises xanthan gum, polyethylene glycol, or is petroleum based.

19. The method of claim 18, wherein the solution, gel or ointment further comprises a non mercaptan reducing agent that comprises a peptide or peptide like molecule.

20. The method of claim 19, wherein the detergent comprises a non mercaptan reducing disulfide moiety.

* * * * *